United States Patent [19]

Derez et al.

[11] Patent Number: 5,382,681

[45] Date of Patent: Jan. 17, 1995

[54] PROCESS FOR THE PRODUCTION OF AN ALKALI METAL CITRATE

[75] Inventors: Frank G. H. Derez, Sint-Pieters-Leeuw; Patrick L. J. Vandervondelen, Eppegem, both of Belgium

[73] Assignee: Cerestar Holding B.V., Sas Van Gent, Netherlands

[21] Appl. No.: 122,300

[22] Filed: Sep. 17, 1993

[30] Foreign Application Priority Data

Oct. 7, 1992 [GB] United Kingdom ............... 9221111

[51] Int. Cl.⁶ ................ C07C 51/42; C07C 51/47; C07C 59/265
[52] U.S. Cl. ................................. 562/580; 562/584
[58] Field of Search ........................ 562/584, 580

[56] References Cited

U.S. PATENT DOCUMENTS

| | | | |
|---|---|---|---|
| 2,362,906 | 11/1944 | Leo et al. | 260/535 |
| 2,697,725 | 12/1954 | Bryce et al. | 260/527 |
| 3,904,684 | 9/1975 | Tsuda et al. | 260/535 P |
| 4,720,579 | 1/1988 | Kulprathipanja | 562/580 |
| 4,924,027 | 5/1990 | Kulprathipanja et al. | 562/580 |
| 5,237,098 | 8/1993 | Bemish et al. | 562/584 |

*Primary Examiner*—José G. Dees
*Assistant Examiner*—Barbara S. Frazier
*Attorney, Agent, or Firm*—Cushman, Darby & Cushman

[57] ABSTRACT

A process for the preparation of an alkali metal citrate which comprises:
  (a) adjusting the pH of an aqueous solution containing citric acid to a value greater than 5.4;
  (b) contacting the aqueous solution with a polymeric adsorbent;
  (c) eluting the resulting charged polymeric adsorbent with an eluant comprising an aqueous solution of a soluble alkali metal hydroxide or alkali metal salt in which the alkali metal corresponds to the alkali metal of the alkali metal citrate to be produced; and
  (d) recovering an aqueous solution of the alkali metal citrate, is disclosed.

12 Claims, No Drawings

PROCESS FOR THE PRODUCTION OF AN ALKALI METAL CITRATE

The present invention relates to a process for the production of an alkali-metal citrate, particularly to the production of an alkali-metal citrate from an aqueous solution, such as a broth containing citric acid obtained by a fermentation process.

Citric acid is produced commercially by the fermentation of a suitable carbohydrate feedstock such as dextrose by a citric acid forming microorganism. The crude product of the fermentation process is an aqueous solution of citric acid together with other organic acids, residual carbohydrate, proteins, amino acids and a range of inorganic salts including cations such as potassium, sodium, calcium, magnesium and iron and anions such as sulphate, chloride, phosphate and nitrate.

Various methods have been proposed for the recovery of pure citric acid from a fermentation broth including precipitation as the calcium salt or adsorption on a suitable adsorbent. Adsorption methods of separation have received considerable attention in recent years and it is to this type of separation that the present invention relates.

A typical method of adsorption separation is described in EP 324 210 A in which an aqueous fermentation product is contacted with a polymeric adsorbent which may be a neutral, cross-linked polystyrene polymer, a nonionic hydrophobic polyacrylic ester polymer, a weakly basic anion exchange resin possessing tertiary amine or pyridine functional groups, or a strongly basic anion exchange resin possessing quaternary amine functional groups. The citric acid is adsorbed on the polymeric adsorbent and is then subsequently desorbed. One strong preference expressed in EP 324 210 A is to conduct the adsorption process at a pH of the aqueous fermentation product which is less than the first ionization constant of citric acid i.e. at a pH effectively less than 3.13. At a pH below this figure all the citric acid will be unionised and will be adsorbed as citric acid and not as a citric acid salt. Above pH 3.13 increasing amounts of citric acid salts will be present giving rise to an increased overall process time because of the longer time required to desorb a mixture of citric acid and citrates rather than citric acid alone.

An alternative adsorption process for recovering citric acid from a fermentation broth is described in Japanese Patent Publication No. 58-164541. In this process the citric acid is separated as its alkali metal salt e.g. as tri-sodium citrate by adsorption on an anion exchange resin of the salt type followed by desorption by means of a mineral acid solution. Example 2 of the Japanese patent publication describes the separation of sodium citrate and glucose using the $SO_4$—form of an anion exchange resin and eluting with 1N sulphuric acid to produce citric acid.

Citric acid is well known for its applications in the food industry but increasingly it is in demand as its tri-sodium salt in the formulation of detergents where the salt acts as a builder and can thus be used to replace phosphate. Tri-sodium citrate also has some food uses, e.g. as a buffering agent, and pharmaceutical applications. In this respect therefore there is an incentive to produce tri-sodium citrate directly as a marketable commodity rather than by converting pure citric acid to the sodium salt. The invention of the present application has therefore the aim of producing citrates, especially tri-sodium citrate from a fermentation broth containing citric acid without the intermediate step of isolating pure citric acid.

According to the invention a process for obtaining an alkali metal citrate is characterized by,
(a) adjusting the pH of an aqueous solution containing citric acid to a value greater than 5.4,
(b) contacting the aqueous solution with a polymeric adsorbent,
(c) eluting the charged polymeric adsorbent with an eluant comprising an aqueous solution of a soluble alkali metal hydroxide or alkali metal salt in which the alkali metal corresponds to the alkali metal of the alkali metal citrate it is the intention to produce and
(d) recovering an aqueous solution of the alkali metal citrate.

Preferably the alkali metal is sodium.

The process of the invention is of greatest utility in enabling an alkali metal citrate to be obtained from the crude aqueous product of a process for citric acid production by fermentation. This crude aqueous product may contain residual carbohydrate feedstock such as dextrose, various salts and protein impurities as well as citric acid in various stages of ionization depending on the pH and the temperature of the fermentation substrate. The pH of the aqueous product is first adjusted to more than 5.4, preferably to about 8.5, suitably by the addition of an alkali e.g. sodium hydroxide. At this pH the citric acid is in the form of mono-, di- and/or tri-alkali metal citrate(s).

The polymeric adsorbent which is used in the process of the invention may be a neutral polymer but is preferably an anion exchange resin particularly a weakly basic anion exchange resin. The polymeric adsorbent is eluted with an aqueous solution of a salt which comprises an alkali metal cation corresponding to that which is to form the alkali metal citrate. The anion component of the eluant salt is less significant but, in the case where the polymeric adsorbent is an anion exchange resin, the anion will become associated with the regenerated resin after removal of the alkali metal citrate therefrom. Suitable anions are sulphate, chloride or hydroxide. The concentration of the alkali metal salt in the eluant is suitably 0.0001 to 7 molar preferably 0.01 to 5 molar.

The solution eluted from the polymeric adsorbent is an aqueous solution of the tri-alkali metal citrate. The tri-alkali metal citrate may be recovered in solid form from the aqueous solution by known means e.g. by crystallisation or evaporation.

The adsorption/desorption stages of the process according to the invention may be carried out at temperatures in the range 20° to 100° C., preferably 20° to 40° C. and at pressures from atmospheric to $20 \times 10^5$ Pas.

The process according to the invention may be carried out batchwise or in a continuous or semi-continuous manner. Preferably, the process is carried out as a countercurrent moving bed or a simulated moving bed countercurrent flow system.

The invention will now be further illustrated with reference to the following Example.

EXAMPLE

The apparatus used was a double jacket chromatography column of height 100 cm and diameter 2.2 cm filled with 343 mls of an anion exchange resin, the sulphate form of AMBERLITE IRA 68 (AMBERLITE is a trade mark).

A pulse test was carried out at 20° C. and atmospheric pressure using a feedstock comprising 25 g tri-sodium citrate and 25 g D(+)glucose mono-hydrate in 200 mls of water. The pH of this solution was about 8.5.

At a total flowrate of 0.3 BV ("bed volume") per hour, 0.02 BV of the feed mixture was injected and subsequently eluted with 3N sodium sulphate solution. During the desorption stage, fractions of 0.032 BV were collected.

The eluted fractions were analyzed by HPLC chromatography, the tri-sodium citrate and glucose contents being as follows:

| Sample No | Time (mins) | Tri-sodium citrate content (mg/l) | Dextrose content (mg/l) |
|---|---|---|---|
| 1 | 95.0 | | 0.9 |
| 2 | 103.0 | | 3.7 |
| 3 | 111.0 | | 7.9 |
| 4 | 119.0 | | 11.9 |
| 5 | 127.0 | | 15.8 |
| 6 | 135.0 | | 18.2 |
| 7 | 143.0 | | 17.1 |
| 8 | 151.0 | | 13.7 |
| 9 | 159.0 | | 9.5 |
| 10 | 167.0 | 1.1 | 6.5 |
| 11 | 175.0 | 1.6 | 3.9 |
| 12 | 183.0 | 2.2 | 2.3 |
| 13 | 191.0 | 3.2 | 1.3 |
| 14 | 199.0 | 4.2 | 0.7 |
| 15 | 207.0 | 5.3 | 0.4 |
| 16 | 215.0 | 6.4 | |
| 17 | 223.0 | 6.9 | |
| 18 | 231.0 | 7.8 | |
| 19 | 239.0 | 7.3 | |
| 20 | 247.0 | 8.1 | |
| 21 | 255.0 | 7.9 | |
| 22 | 263.0 | 6.9 | |
| 23 | 271.0 | 6.3 | |
| 24 | 279.0 | 5.5 | |
| 25 | 287.0 | 4.7 | |
| 26 | 295.0 | 4.1 | |
| 27 | 303.0 | 3.3 | |
| 28 | 311.0 | 3.1 | |
| 29 | 319.0 | 2.5 | |
| 30 | 327.0 | 2.1 | |
| 31 | 335.0 | 1.9 | |
| 32 | 343.0 | 1.6 | |

We claim:
1. A process for the preparation of an alkali metal citrate which comprises:
    (a) adjusting the pH of an aqueous solution containing citric acid to a value greater than 5.4,
    (b) contacting the aqueous solution with a polymeric adsorbent,
    (c) eluting the resulting charged polymeric adsorbent with an eluant comprising an aqueous solution of a soluble alkali metal hydroxide or alkali metal salt in which the alkali metal corresponds to the alkali metal of the alkali metal citrate to be produced, and
    (d) recovering an aqueous solution of the alkali metal citrate.

2. A process as set forth in claim 1 in which the pH of the solution containing citric acid is adjusted to a value of about 8.5.

3. A process as set forth in claim 1 in which the alkali metal citrate is tri-sodium citrate.

4. A process as set forth in claim 1 in which the aqueous solution containing citric acid is the crude aqueous product of a process for the production of citric acid by fermentation.

5. A process as set forth in claim 1 in which the polymeric adsorbent is an anion exchange resin.

6. A process as set forth in claim 5 in which the anion exchange resin is a weakly basic anion exchange resin.

7. A process as set forth in claim 5 in which the anion exchange resin is in the sulphate form.

8. A process as set forth in claim 1 in which the eluant is an aqueous solution of sodium sulphate.

9. A process as set forth in claim 1 in which the concentration of the alkali metal salt in the recovered alkali metal salt solution is 0.0001 to 7 molar.

10. A process as set forth in claim 5 in which steps (b) and (c) are carried out at a temperature in the range 20° C. to 100° C.

11. A process as set forth in claim 5 in which steps (b) and (c) are carried out at a pressure in the range of atmospheric pressure to $20 \times 10^5$ Pas.

12. A process as set forth in claim 5 which is carried out as a countercurrent moving bed or a simulated moving bed countercurrent flow system.

* * * * *